United States Patent [19]

Meyer et al.

[11] Patent Number: 5,744,057
[45] Date of Patent: Apr. 28, 1998

[54] POLYMERIZABLE, CHIRAL COMPOUNDS, AND USE THEREOF

[75] Inventors: Frank Meyer, Ludwigshafen; Karl Siemensmeyer; Karl-Heinz Etzbach, both of Frankenthal; Peter Schuhmacher, Mannheim, all of Germany

[73] Assignee: BASF Aktiengesellshaft, Ludwigshafen, Germany

[21] Appl. No.: 658,560

[22] Filed: Jun. 5, 1996

[30] Foreign Application Priority Data

Jun. 9, 1995 [DE] Germany ............... 195 20 704.1

[51] Int. Cl.$^6$ ............... C09K 19/52; C09K 19/32; G02F 1/13; C07D 493/00
[52] U.S. Cl. ............... 252/299.01; 252/299.61; 252/299.62; 252/299.67; 349/183; 549/464
[58] Field of Search ............... 252/299.01, 299.2, 252/299.61, 299.64, 299.62, 299.63, 299.67; 549/464; 349/182, 183

[56] References Cited

U.S. PATENT DOCUMENTS

| | | | |
|---|---|---|---|
| 4,997,591 | 3/1991 | Heppke et al. | 252/299.61 |
| 5,326,495 | 7/1994 | Eidenschink | 252/299.01 |
| 5,350,873 | 9/1994 | Bach et al. | 560/60 |
| 5,417,882 | 5/1995 | Bach et al. | 252/299.1 |
| 5,417,884 | 5/1995 | Etzbach et al. | 252/299.61 |
| 5,455,325 | 10/1995 | Bach et al. | 528/272 |

FOREIGN PATENT DOCUMENTS

| | | |
|---|---|---|
| 39 17 196 | 12/1990 | Germany. |
| 43 42 280 | 6/1995 | Germany. |

OTHER PUBLICATIONS

Liquid Crystals & Plastic Crystals, vol. 1, 5 Pages, G.W. Gray, "Physico–Chemical Properties And Methods Of Investigation", 1974.

Advances in Solid State Physics, p. 99, 1971, Heinz Baessler, "Liquid Crystals".

The Journal of Chemical Physics, vol. 52, pp. 631–637, Jan. 1–Jun. 15, 1970, H. Baessler, et al., "Helical Twisting Power Of Steroidal Solutes In Cholesteric Mesophases".

J.G. Heft, vol. 12, pp. 599–602, 1971, H. Stegemeyer, et al., "Induzierung Von Optischer Aktivitat Und Zirkulardichroismus In Nematischen Phasen Durch Chirale Molekule" (English Abstract).

Phys. Chem., vol. 78, pp. 869–874, 1974, Von H. Finklemann, et al., "Beschreibung Cholesterischer Mischsysteme Mit Einer Erweiterten Goossens–Theorie".

Molecular Crystals and Liquid Crystals, vol. 16, pp. 33–37, 1972, James Adams, et al., "The Relationship Between Pitch Change and Stimulus in Cholesterics".

Makromol Chem., vol. 187, pp. 289–296, 1986, Giancarlo Galli, "Synthesis And Thermotropic Properties Of New Mesogenic Diacrylate Monomers".

Mol. Cryst. Liq. Cryst., vol. 203, pp. 113–126, 1991, I. Heynderickx, et al., "The Use Of Cholesterically–Ordered Polymer Networks In Practical Applications".

Primary Examiner—Shean C. Wu
Attorney, Agent, or Firm—Oblon, Spivak, McClelland, Maier & Neustadt, P.C.

[57] ABSTRACT

A polymerizable, chiral compound of the formula (I):

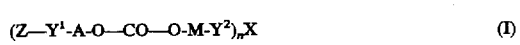

$$(Z-Y^1-A-O-CO-O-M-Y^2)_n X \qquad (I)$$

where:

A, M, $Y^1$ and $Y^2$, X, n and Z are as defined herein; and which compound is suitable for use in electro-optical displays or as chiral dopes for nematic or cholesteric liquid crystals for the production of layers which reflect in colors.

17 Claims, No Drawings

POLYMERIZABLE, CHIRAL COMPOUNDS, AND USE THEREOF

BACKGROUND OF THE INVENTION

The invention relates to polymerizable, chiral compounds of the formula I $$(Z-Y^1-A-O-CO-O-M-Y^2)_n X \qquad I$$

where

A is a spacer,

M is a mesogenic group, $Y^1$ and $Y^2$ are chemical bonds or —O—, —S—, —CO—O—, —O—CO—, —O—CO—O—, —CO—N(R)— or —N(R)—CO—, X is an n-valent chiral radical, R is hydrogen or $C_1$–$C_4$-alkyl, n is from 2 to 6,

Z $a_1$) at least one of these radicals is a reactive group which can participate in a polyaddition reaction, $a_2$) at least two of these radicals are substituents carrying a reactive group which can participate in a polycondensation reaction, b) is hydrogen or an unreactive radical so long as condition ($a_1$) or ($a_2$) is satisfied, where Z, $Y^1$, A, M and $Y^2$, since they occur n times in I, can be identical or different.

The present invention furthermore relates to the use of these compounds in electro-optical displays or as chiral dopes for nematic or cholesteric liquid crystals, in particular for the production of layers which reflect in colors.

DESCRIPTION OF THE BACKGROUND

It is known that molecules which are anisotropic in shape can form liquid-crystalline phases, known as mesophases, on warming. The individual phases differ in the spatial arrangement of the major part of the molecules on the one hand and in the molecular arrangement with respect to the long axes on the other hand (G. W. Gray, P. A. Winsor, Liquid Crystals and Plastic Crystals, Ellis Horwood Limited, Chichester, 1974). The nematic liquid-crystalline phase is distinguished by the fact that there is only one alignment long-distance order due to the long molecular axes lining up in parallel. Under the prerequisite that the molecules making up the nematic phase are chiral, a cholesteric phase forms, in which the long axes of the molecules form a helical superstructure perpendicular thereto (H. Baessler, Festkörperprobleme XI, 1971). The chiral moiety may be present in the liquid-crystalline molecule itself or added to the nematic phase as a dope. Phases generated by doping are referred to as induced-cholesteric phases. This phenomenon was first studied in cholesterol derivatives (see, for example, H. Baessler, M. M. Labes, J. Chem. Phys. 52 (1970) 631). Later, the induction of cholesteric phases also became possible through addition of other chiral substances which are not themselves liquid-crystalline (H. Stegemeyer, K. J. Mainusch, Naturwiss. 58 (1971) 599; H. Finkelmann, H. Stegemeyer, Ber. Bunsenges. Phys. Chem. 78 (1974) 869).

The cholesteric phase has remarkable optical properties: a large optical rotation and pronounced circular dichroism caused by selective reflection of circular-polarized light within the cholesteric layer. The different colors to be observed depending on the viewing angle depend on the pitch of the helical superstructure, which is itself dependent on the twisting power of the chiral component. The pitch and thus the wavelength range of the selectively reflected light of a cholesteric layer can be varied, in particular by changing the concentration of a chiral dope (J. E. Adams, W. E. L. Haas, Mol. Cryst. Liq. Cryst. 16 (1972) 33). Such cholesteric systems offer interesting opportunities for practical use. Thus, incorporation of chiral moieties into mesogenic acrylic esters after establishment of the cholesteric alignment and photocrosslinking can give a stable, colored network, but the concentration of the chiral component therein cannot be changed (G. Galli, M. Laus, A. Angeloni, Makromol. Chem. 187 (1986) 289). Furthermore, admixing of non-crosslinkable, chiral compounds with nematic acrylic esters after photocrosslinking can give a colored polymer (I. Heynderickx, D. J. Broer, Mol. Cryst. Liq. Cryst. 203 (1991) 113), but this still contains volatile constituents which are prohibitive for industrial application.

The earlier German Patent Application P 43 42 280.2 describes similar polymerizable chiral compounds which are suitable for the preparation of cholesteric liquid-crystalline polymers and which differ from the novel compounds essentially that the spacer A and the mesogenic group M are linked by groups other than carbonate.

SUMMARY OF THE INVENTION

It is an object of the present invention to synthesize novel chiral compounds which firstly have a high twisting power and secondly can be incorporated into the cholesteric phase in a stable manner over a broad concentration range without diffusing out of the phase or crystallizing.

DETAILED DESCRIPTION OF THE PREFERRED EMBODIMENTS

We have found that this object is achieved by the polymerizable chiral compounds defined at the outset.

The moieties Z and A, and M and X present in the novel compounds are linked to one another via bridges $Y^1$ and $Y^2$ respectively, such as —O—, —S—, —CO—O—, —O—CO—, —O—CO—O—, —CO—N(R)— or —N(R)—CO—, or via a direct bond, the spacer A being linked to the mesogenic group via a carbonate group (—OCOO—). Chiral polymerizable compounds containing such a carbonate group have the advantageous property of having particularly low phase-transition temperatures and are thus particularly suitable for applications at room temperature.

Suitable spacers A are all groups known for this purpose. Spacers generally contain from 2 to 30, preferably from 2 to 12, carbon atoms and comprise linear aliphatic groups. They can be interrupted in the chain, for example, by O, S, NH or $NCH_3$, but these groups must not be adjacent. Suitable substituents for the spacer chain are fluorine, chlorine, bromine, cyano, methyl and ethyl.

Examples of representative spacers are the following:

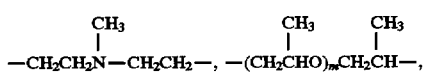

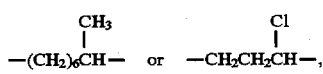

where m is from 1 to 3 and p is from 1 to 12.

M can be any known mesogenic groups. Particularly suitable groups are those of the formula Ia $$-(-T-Y^3-)_r-T- \qquad Ia$$

where

T are divalent isocycloaliphatic, heterocycloaliphatic, isoaromatic or heteroaromatic radicals, $Y^3$ are bridging members as defined for $Y^1$ or are —$CH_2$—O—, —O—$CH_2$—, —CH=N— or —N=CH—; and r is from 0 to 3, where T and $Y^3$, in the case where r is >0 or r is >1, can be identical or different.

r is preferably 0 or 1.

T can also be a ring system substituted by fluorine, chlorine, bromine, cyano, hydroxyl or nitro. T is preferably one of the following:

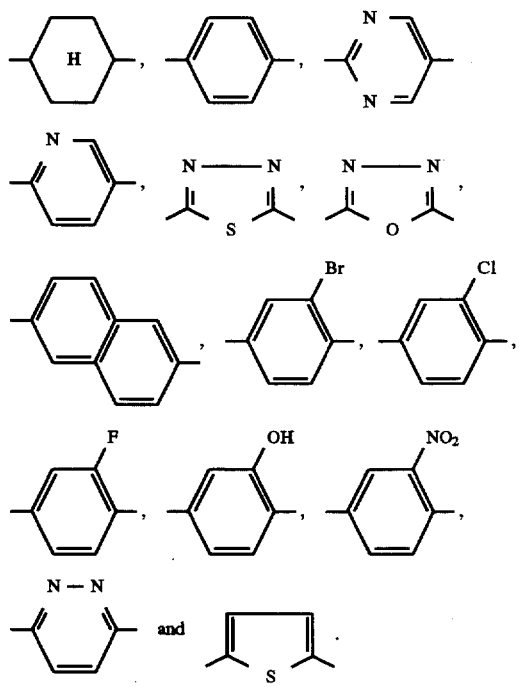

The mesogenic group M is particularly preferably one of the following:

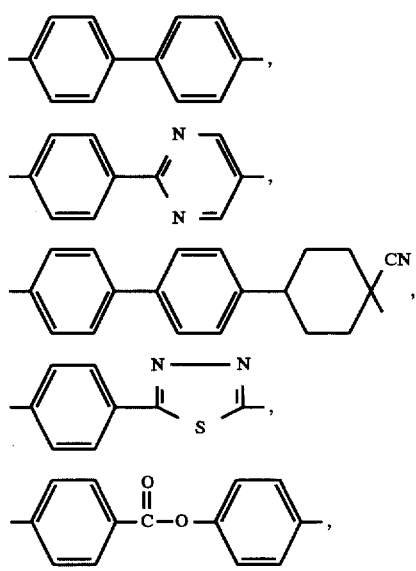

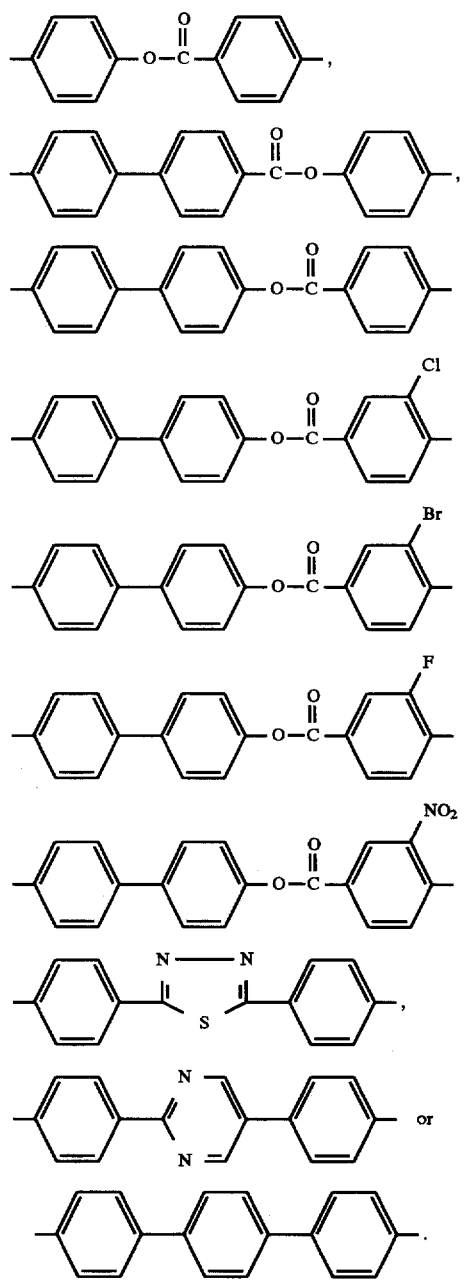

n in the formula I is preferably 2 or 3, in particular 2.

Of the chiral radicals X, availability reasons means that particular preference is given to those derived from sugars, binaphthyl or biphenyl derivatives and optically active glycols, dialcohols or amino acids. In the case of sugars, particular mention should be made of pentoses and hexoses and derivatives thereof.

Individual examples of radicals X are the following:

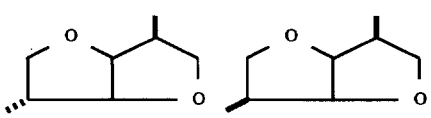

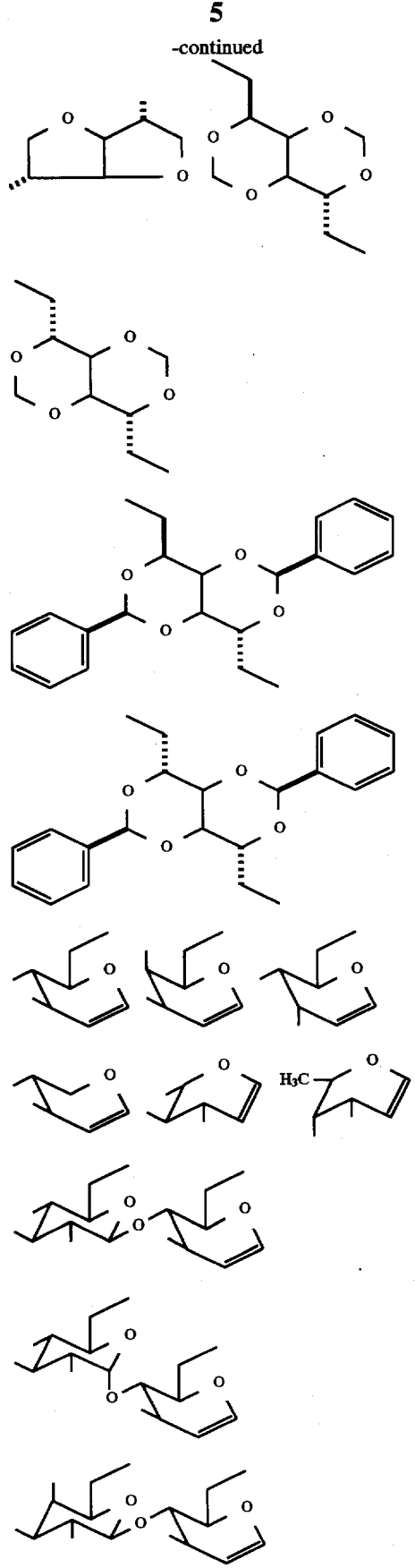
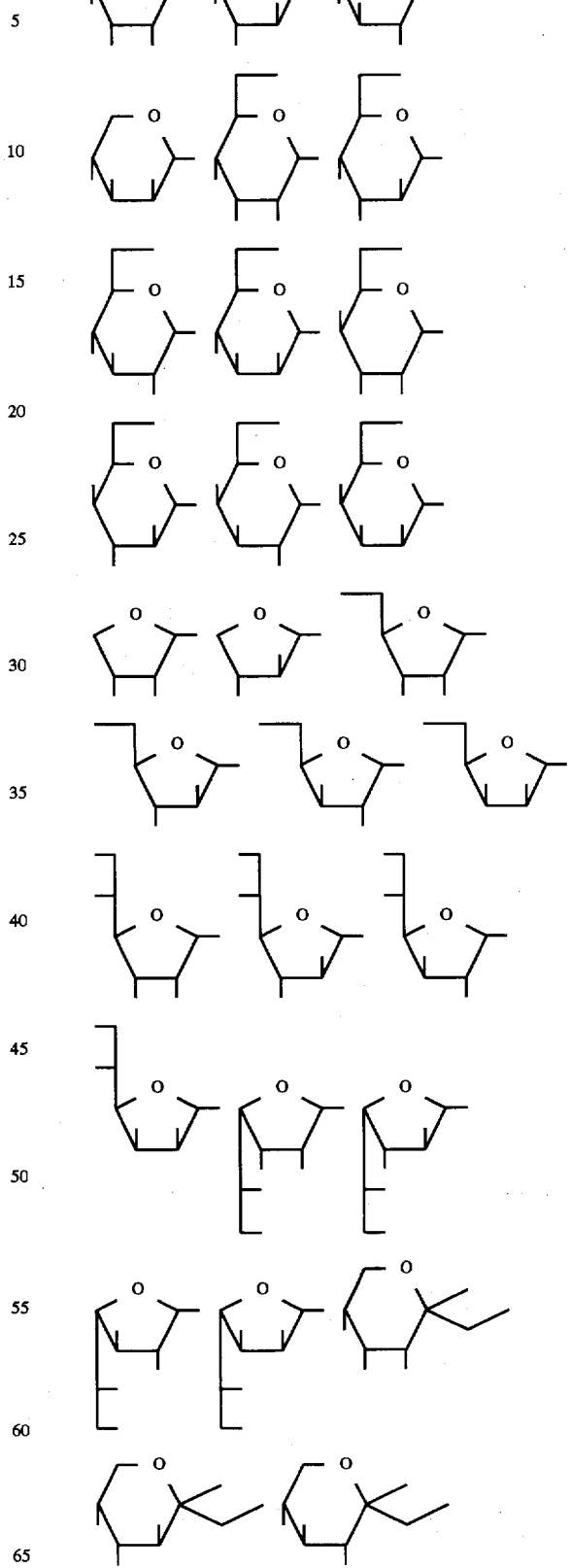

-continued
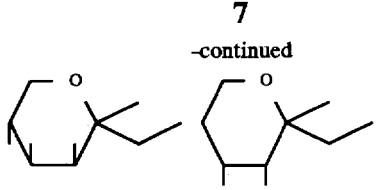
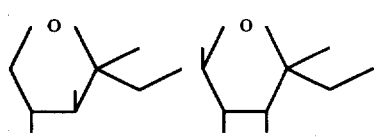
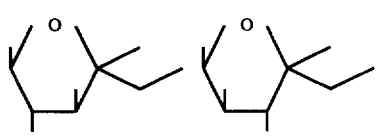
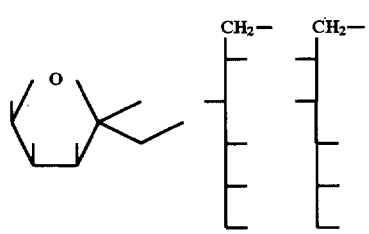
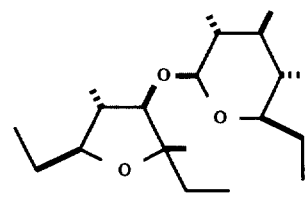
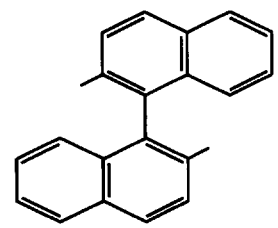
-continued
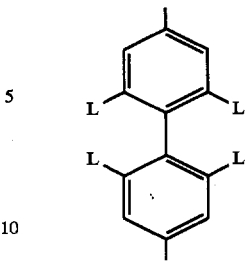
where
L is $C_1$- to $C_4$-alkyl, $C_1$–$C_4$-alkoxy, halogen, COOR, OCOR, CONHR or NHCOR, where R is as defined above.
(The terminal dashes in the above formulae indicate the free valences).
Particular preference is given to the following, for example:
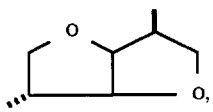
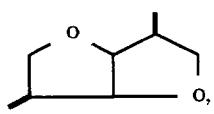
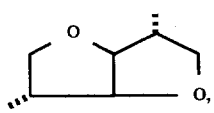
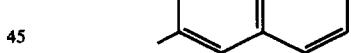
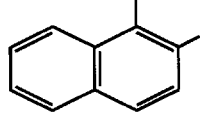
or
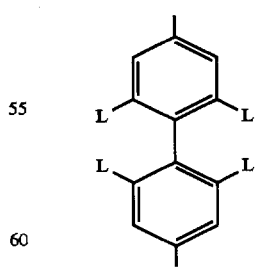
Optically active glycols or derivatives thereof conform, for example, to the formula

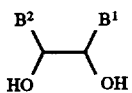

where

B¹ and B², independently of one another, are $C_1$- to $C_4$-alkyl, which may be substituted by hydroxyl and interrupted by —O—, phenyl or unsubstituted or substituted carboxyl, and one of B¹ and B² can also be hydrogen, where, in the case of identical radicals B¹ and B², the R,S configuration is excluded.

Individual examples of such radicals B¹ and B² are —CO₂CH₃, —CO₂CH₂CH₃, —CO₂(CH₂)₂CH₃, —CO₂(CH₂)₃CH₃, —CO₂CH(CH₃)₂, —CO₂C(CH₃)₃ or —CH(OH)CH₂(OH).

Also suitable as X are divalent chiral groups having the following structures:

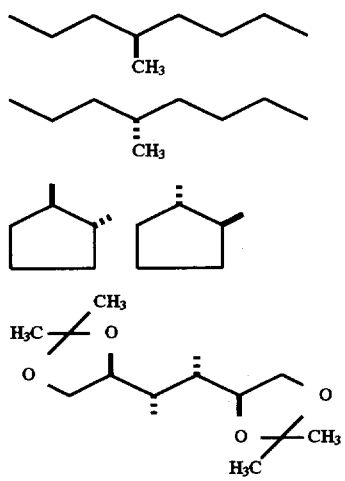

Preferred radicals Z are the following:

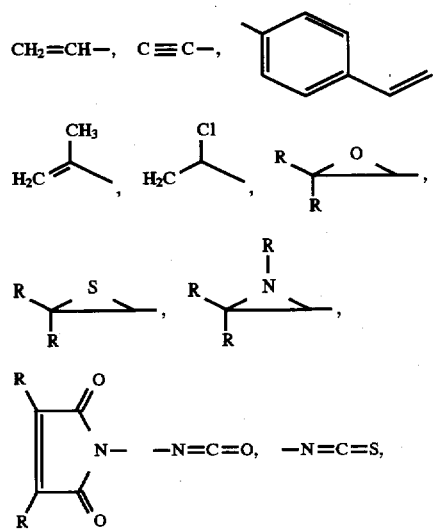

—O—C≡N, —COOH, —OH or —NH₂, where the radicals R may be identical or different. Of the reactive polymerizable groups, the cyanates can be spontaneously trimerized to give cyanurates and are therefore preferred. Polymerization of the other groups mentioned requires further compounds containing complementary reactive groups. For example, isocyanates can polymerize with alcohols to give urethanes and with amines to give urea derivatives. An analogous situation applies to thiiranes and aziridines. Carboxyl groups can be condensed to give polyesters and polyamides. The maleimido group is particularly suitable for free-radical copolymerization with olefinic compounds such as styrene. The complementary reactive groups can either be present in a second novel compound which is mixed with the first or can be introduced into the polymerization mixture via auxiliary compounds containing 2 or more of these complementary groups.

Since novel compounds of the formula I in which at least two radicals Z are reactive groups which can undergo a polycondensation or polyaddition reaction give particularly stable polymer films, these are particularly preferred.

In addition to hydrogen, suitable unreactive radicals Z which may be constituents of the novel compounds of the formula I, so long as at least one radical Z is a reactive radical, are $C_1$–$C_{20}$-alkyl radicals, in particular linear $C_1$–$C_{12}$-alkyl radicals.

The chiral starting compounds for the moiety X, generally hydroxyl compounds $X(OH)_n$, are for the most part commercially available.

The novel units Z—Y¹-A-O—CO—O-M-Y² can be obtained by syntheses known in general terms, as described, for example, in DE-A 39 17 196.

The groups Z, A, M and X are preferably coupled to one another by condensation reactions, forming the desired bridges Y¹ and Y², ie. an ester bond is formed, for example, by reaction of a mesogen carboxylate with a chiral hydroxyl compound or an ether bond is formed by condensation of two hydroxyl groups, after appropriate activation, etc. The carbonate group is preferably formed by successive reaction of phosgene with a hydroxyl-substituted compound Z—Y¹-A-OH and a compound HO-M or $(HO-M-Y^2)_nX$.

The novel compounds are particularly suitable for use in electro-optical display elements or as chiral dopes for nematic or cholesteric liquid crystals, in particular for the production of layers which reflect in colors.

EXAMPLE 1

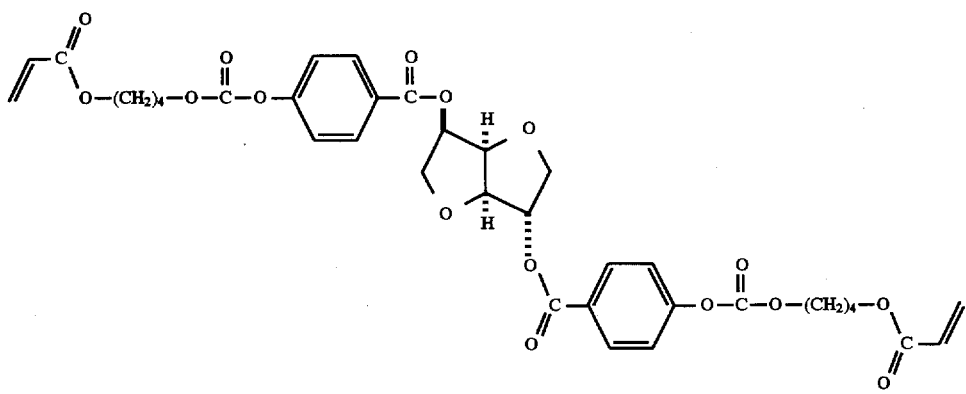

3.5 g (9.1 mmol) of bis(4'-hydroxybenzoyl)isosorbitol and 4.15 g (20.1 mmol) of 4-acryloxybutoxycarbonyl chloride (prepared in a known manner from 4-acryloxybutanol and phosgene) in 100 ml of pyridine/dichloromethane (1:1 vol:vol) were reacted at 3° C. The mixture was then stirred at room temperature for 15 hours, washed twice with dilute hydrochloric acid and three times with water and dried over $Na_2SO_4$. After distillation of the solvent, the product was purified by chromatography.

Yield: 24%.

Melting point: 43° C.

Helical Twisting Power (HTP): 34 µm$^{-1}$ (The HTP was determined by the method described by H. Finkelmann and H. Stegemeyer in Ber. Bunsenges. Phys. Chem. 78, (1974) 869).

EXAMPLE 2

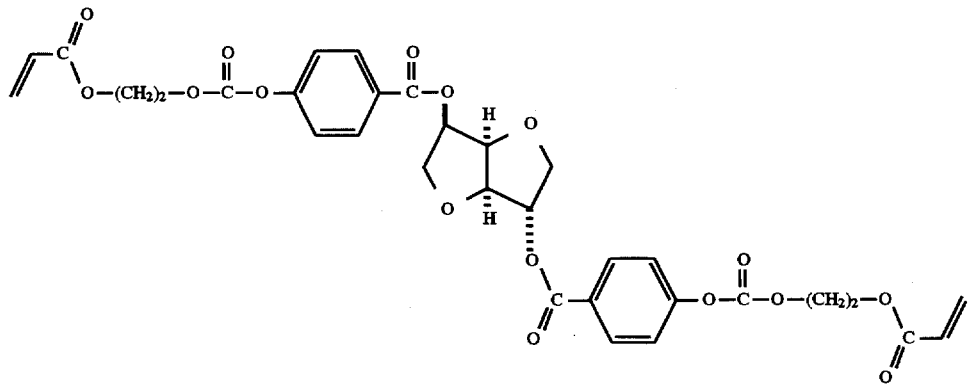

The compound of Example 2 was prepared by a method similar to that of Example 1.

We claim:

1. A polymerizable, chiral compound of the formula $$(Z-Y^1-A-O-CO-O-M-Y^2)_n X \qquad \text{I}$$

where

A is a spacer,

M is a mesogenic group, $Y^1$ and $Y^2$ are chemical bonds or —O—, —S—, —CO— O—, —O—CO—, —O—CO—O—, —CO—N(R)— or —N(R)—CO—, X is an n-valent chiral radical, R is hydrogen or $C_1$–$C_4$-alkyl, n is from 2 to 6,

Z a1) at least one of these radicals is a reactive group which can participate in a polyaddition reaction, a2) at least two of these radicals are substituents carrying a reactive group which can participate in a polycondensation reaction, b) is hydrogen or an unreactive radical so long as condition (a1) or (a2) is satisfied, where Z, $Y^1$, A, M and $Y^2$, since they occur n times in I, can be identical or different.

2. The compound of the formula I as claimed in claim 1, where n has the value 2.

3. The compound of the formula I as claimed in claim 1, where the mesogenic group M is a group of the formula Ia:

$$-(T-Y^3)_r-T- \qquad \text{(Ia)}$$

where:

T are divalent isocycloaliphatic, heterocycloaliphatic, isoaromatic or heteroaromatic radicals, $Y^3$ are bridging members as defined for $Y^1$ or are —$CH_2$—O—, —O—$CH_2$—, —CH=N— or —N=CH—, and r is from 0 to 3, where T and $Y^3$ are identical or different.

4. The compound of the formula I as claimed in claim 3, where r has the value 0 or 1.

5. The compound of the formula I as claimed in claim 2, where X is one of the following groups:

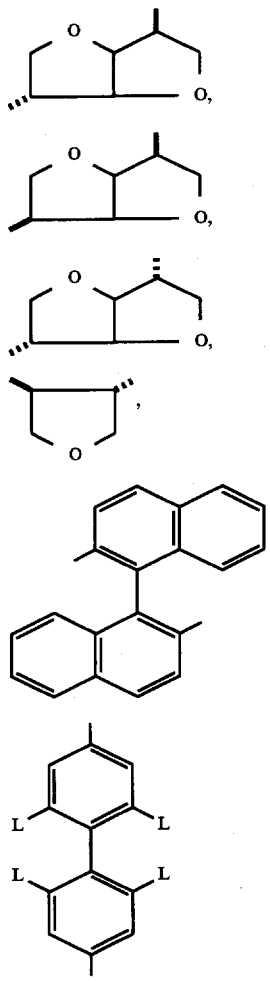

or

L are identical or different substituents from the series consisting of $C_1$–$C_4$-alkyl, $C_1$–$C_4$-alkoxy, halogen, —CO—OR, —O—CO—R, —CO—NH—R and —NH—CO—R.

6. The compound of the formula I as claimed in claim 1, where at least one of the Z—$Y^1$— groups is a cyanate or isocyanate group, in which case $Y^1$ is a chemical bond.

7. The compound of the formula I as claimed in claim 1, where at least one of the radicals Z is an epoxide group or a radical carrying an epoxide group.

8. The compound of the formula I as claimed in claim 1, where Z, $Y^1$, A, M, $Y^2$, R and L are in each case identical.

9. An electro-optical liquid-crystal display device, comprising a compound of the formula I as claimed in claim 1.

10. A process for doping liquid crystals, wherein a compound of the formula I as claimed in claim 1 is mixed with nematic or cholesteric liquid crystals.

11. A process for producing cholesteric liquid-crystalline layers which reflect in colors by doping liquid crystals with chiral dopes of the general formula I as claimed in claim 1.

12. The compound of claim 1, wherein Z is $CH_2CH$—.

13. The compound of claim 1 having the formula:

where

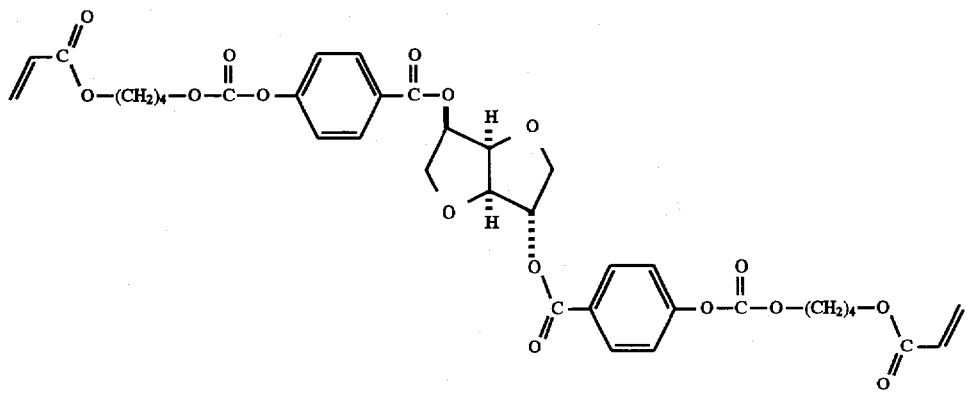

14. The compound of claim 1 having the formula:

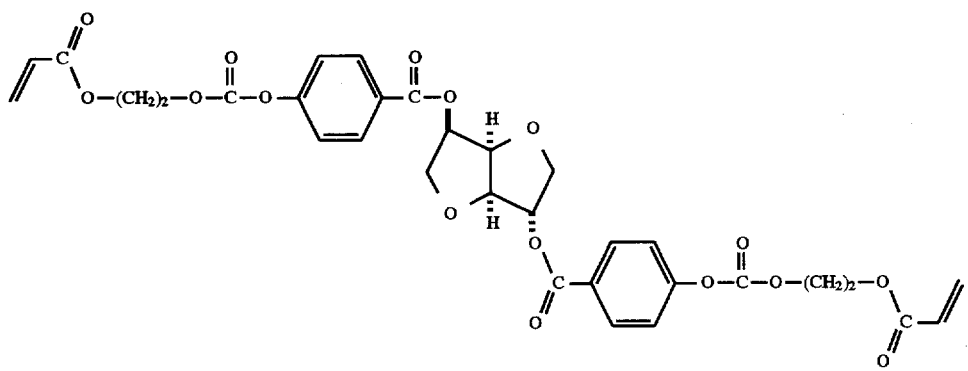
15. The compound of claim 1, wherein T is selected from the group consisting of ring systems having the formulae:
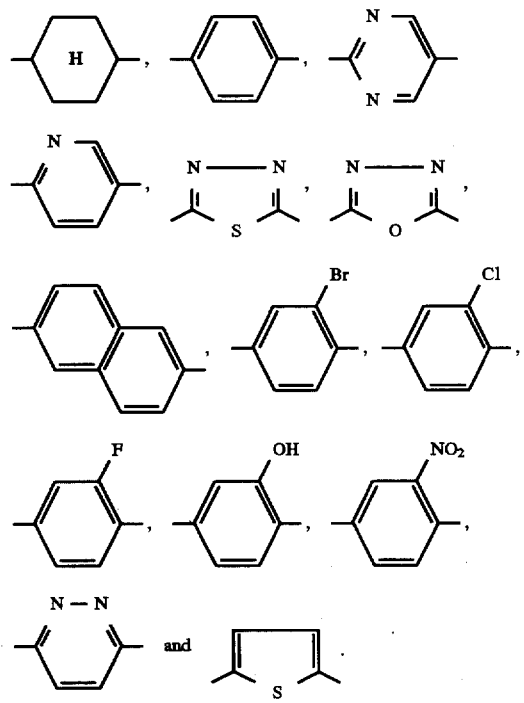
16. The compound as claimed in claim 1, where said mesogenic group M is selected from the group of ring systems having the formulae:
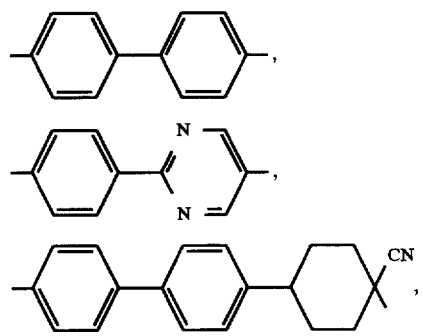
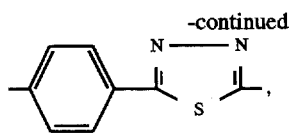
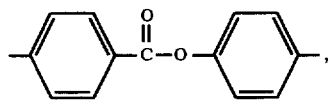
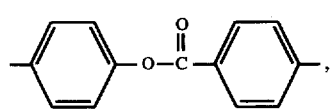
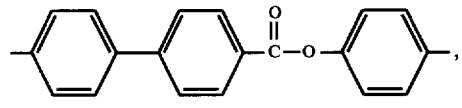
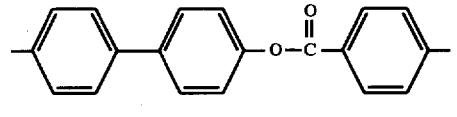
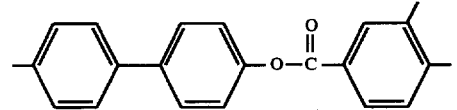
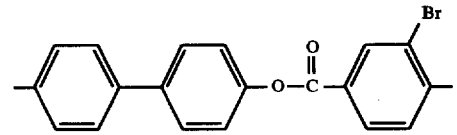
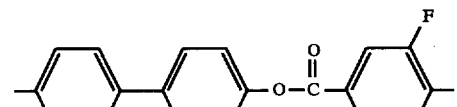
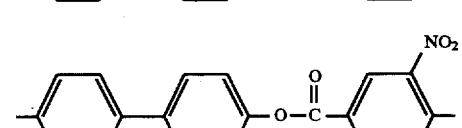

-continued
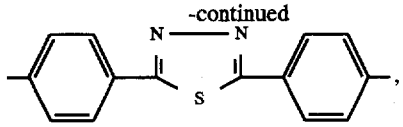
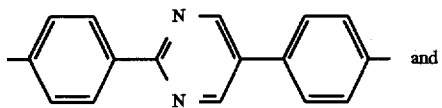
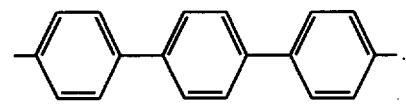
17. The compound as claimed in claim 1, wherein Z is selected from the group consisting of radicals of the formulae:
$H_2=CH-$, $H_2\equiv C-$, 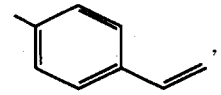
-continued
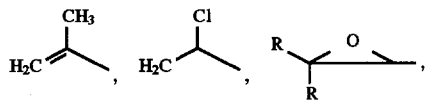
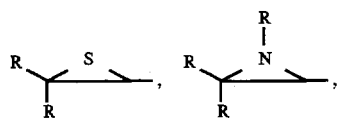
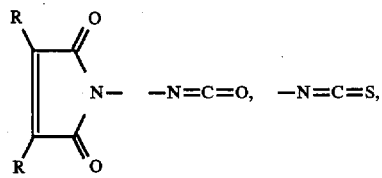
$-O-C\equiv N$, $-COOH$, $-OH$ and $-NH_2$,
* * * * *